United States Patent [19]

Beadle et al.

[11] Patent Number: 5,215,591
[45] Date of Patent: Jun. 1, 1993

[54] CRYSTALLINE FORM OF D-GULOSE

[75] Inventors: James R. Beadle, Elkridge; Gilbert V. Levin, Annapolis; Lee R. Zehner, Brookeville, all of Md.

[73] Assignee: Biospherics Incorporated, Beltsville, Md.

[21] Appl. No.: 856,638

[22] Filed: Mar. 24, 1992

Related U.S. Application Data

[63] Continuation-in-part of Ser. No. 658,879, Feb. 22, 1991, abandoned.

[51] Int. Cl.$^5$ .................. C13F 3/00; C13F 13/00; C13F 1/02
[52] U.S. Cl. .......................... 127/30; 127/58; 127/60
[58] Field of Search .................. 127/30, 58, 60

[56] References Cited

U.S. PATENT DOCUMENTS

| | | |
|---|---|---|
| 3,454,425 | 7/1969 | Smythe et al. .................. 127/64 |
| 3,607,392 | 9/1971 | Lauer et al. .................. 127/30 |
| 4,421,568 | 12/1983 | Huibers .................. 127/30 |
| 4,963,382 | 10/1990 | Arena et al. .................. 127/30 |

Primary Examiner—Theodore Morris
Assistant Examiner—P. L. Hailey
Attorney, Agent, or Firm—William S. Ramsey

[57] ABSTRACT

Free flowing, substantially pure, non-hygroscopic, crystalline β-D-gulopyranose is disclosed. This crystalline form of D-gulose is characterized by a sharp melting point of 130°–132° C., a specific optical rotation of −40° and characteristic mutarotation. A method for preparation of crystalline β-D-gulopyranose from D-gulose syrup is also disclosed. This method involves dilution of the D-gulose syrup, followed by initiation of crystallization, and isolation of β-D-gulopyranose crystals. Crystalline β-D-gulopyranose may be used as an excipient, a chelating agent, a pharmaceutical intermediate, a cleaning agent for glass and metals, a food additive, and as an additive for detergents.

8 Claims, 2 Drawing Sheets

MUTAROTATION OF D-GULOSE
(c = 20 g/100mL, Temp = 20 C)

D-GULOSE MUTAROTATION FIRST ORDER PLOT

CRYSTALLINE FORM OF D-GULOSE

This application is a continuation-in-part of application Ser. No. 658,879, filed Feb. 22, 1991, now abandoned.

FIELD OF THE INVENTION

The present invention relates to crystalline β-D-gulopyranose, a novel form of the hexose sugar D-gulose.

BACKGROUND OF THE INVENTION

D-Gulose was first prepared by Emil Fischer in 1891. [Fischer, et al, Ber., 24, 532 (1891)] During the past 100 years, several other syntheses of D-gulose have been reported, including the following: van Ekenstein, Blanksma, Rec. Trav. Chim., 27, 3 (1908); Meyer zu Reckendorf, Angew. Chem. Int. Ed., 6, 177 (1967); Köster, et al. Angew. Chem. 92, 553 (1980).

D-Gulose is an aldohexose sugar which does not occur in nature. Since no natural source of the sugar exists, its preparation by artificial means is required. One obstacle to the commercial development of D-gulose has been that a crystalline, free flowing, highly pure highly pure form of D-gulose has not been previously known. The Merck Index, Tenth Edition, 4459–4460 (1983) discloses that D-gulose is a syrup.

Many monosaccharides are known to exist in multiple crystalline forms which vary with respect to physical and chemical properties. For example, the common sugar D-glucose exists in two different isomeric forms, α-D-glucopyranose and β-D-glucopyranose.

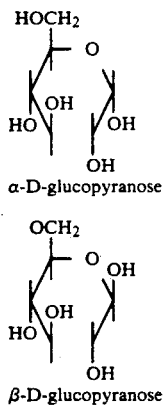

Both D-glucose isomers have been isolated in pure form. Although they do not differ in elementary composition, their physical and chemical properties differ as shown in the following table:

TABLE
PROPERTIES OF α- AND β-D-GLUCOPYRANOSE

| PROPERTY | α-D-glucopyranose | β-D-glucopyranose |
|---|---|---|
| Specific rotation | +112.2° | +18.7° |
| Melting point, °C. | 146 | 150 |
| Solubility in H$_2$O, g per 100 mL | 82.5 | 178 |
| Relative rate of oxidation by glucose oxidase | 100 | <1.0 |

Taste and sweetness level is also a function of the crystalline form of a sugar. For example, crystalline α-D-mannopyranose is about half as sweet as glucose. On the other hand, crystalline β-D-mannopyranose is distinctly bitter. Also, crystalline β-D-fructopyranose tastes almost twice as sweet as sucrose while an aqueous solution of D-fructose, which exists as a mixture of several isomeric forms, is approximately equal to the sweetness of sucrose.

The novel crystalline D-gulose of this invention has been determined to consist entirely of the pure isomer β-D-gulopyranose. In this crystalline form, β-D-gulopyranose has been found to possess many desirable features which were not available from syrupy D-gulose. For example, it is free flowing, non-hygroscopic, highly pure and has a clean sweet taste. In this form, β-D-gulopyranose is useful, for example, as an excipient, a chelating agent, a pharmaceutical intermediate, a cleaning agent for glass and metals, a food additive, and as an additive for detergents.

In such applications, it is a very desirable feature to have a crystalline, free flowing form of D-gulose. For example, as an excipient, crystalline β-D-gulopyranose may be combined with an active drug for preparing a convenient, agreeable dosage form, such as a tablet. As a food additive, crystalline D-gulose can be used in applications such as dry, prepared mixes for making beverages, cakes puddings and the like. As a pharmaceutical intermediate, crystalline β-D-gulopyranose may be used in chemical processes where water is detrimental or where high purity is required to avoid formation of toxic by-products.

In the preparation of D-gulose by Köster, et at, Angew. Chem., 92(7) 553 (1980), the final product obtained was a water free glassy solid which could be ground to a very hygroscopic white powder. The powder softened over a broad temperature range (60°–80° C.) to give a clear melt at 80° C. Another solid was obtained by precipitating the D-gulose from ethanol with diethyl ether, but no melting range or other physical properties are given for this second product.

Van Hook and Mac Innes, Sugar Journal, 16(5), 20(1953) describes the crystallization by sonic irradiation of several sugars including arabinose, fructose, sorbitol, gulose, and others. In this article no physical properties are given and it is not specified whether D-gulose or L-gulose was crystallized.

SUMMARY OF THE INVENTION

It has now been found that a crystalline, free flowing, non-hygroscopic form of β-D-gulopyranose may be obtained. Crystalline β-D-gulopyranose is characterized by a sharp melting point of 130°–132° C., a specific optical rotation of −40° and characteristic mutarotation.

DETAILED DESCRIPTION OF THE INVENTION

Figure 1:
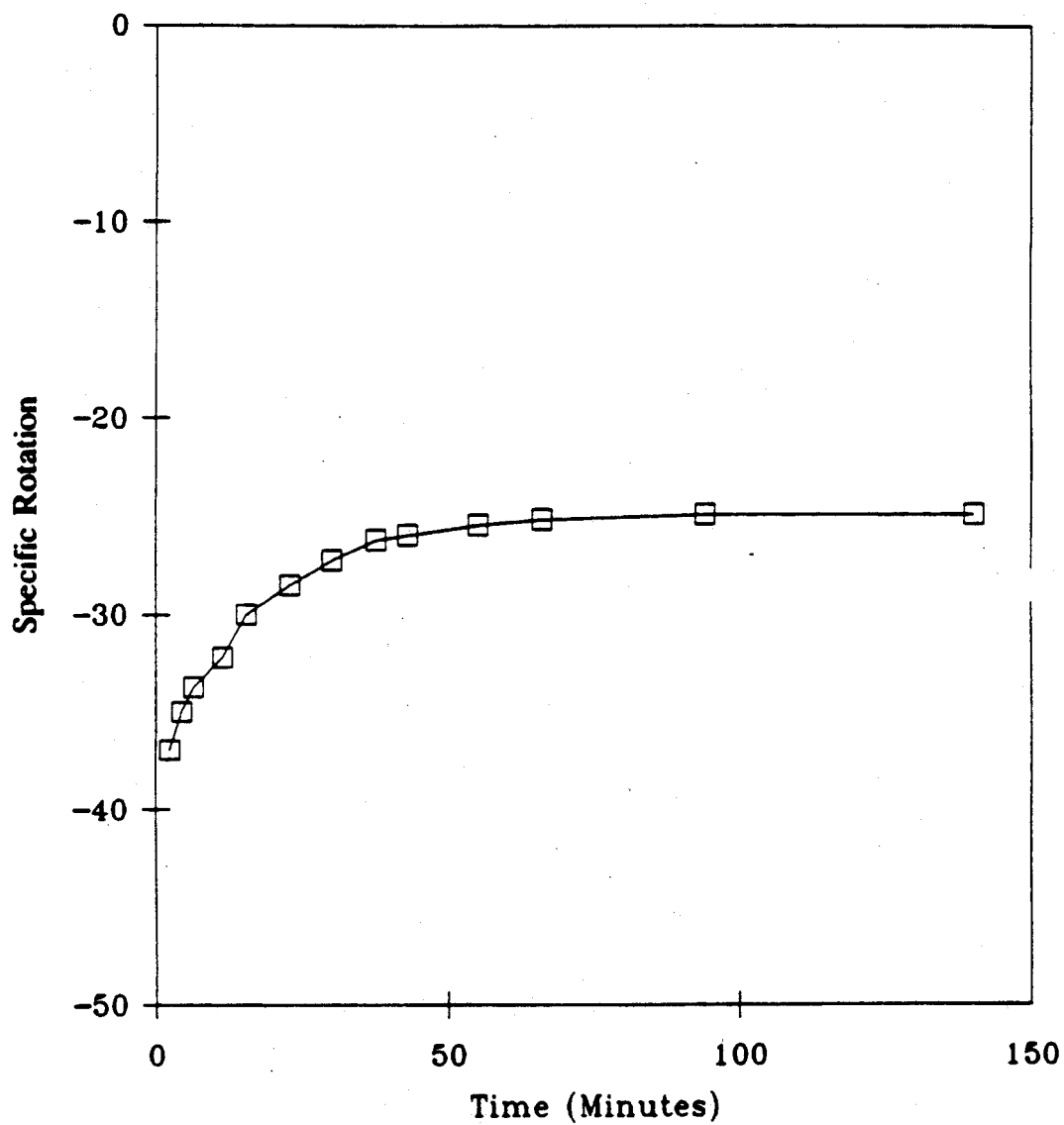
FIG. 1 shows the mutarotation of crystalline β-D-gulopyranose.

The term β-D-gulopyranose as used herein is used within the meaning of the standard terminology of carbohydrate chemistry to refer to the hexose monosaccharide which has been assigned the Chemical Abstract Registry Number 7283-08-1. This isomer is clearly distinguished from other D-gulose isomers in the chemical literature. For example, D-glucose and α-D-gulopyranose are assigned Chemical Abstract Registry Numbers 4205-23-6 and 7282-78-2, respectively. β-D-Gulopyranose is represented by the following Haworth structural formula:

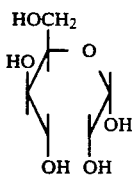

Crystalline β-D-gulopyranose is obtained by diluting D-gulose in syrup form with absolute ethanol, water, or some other suitable solvent, initiating crystallization, and stirring until crystallization is complete. In the case where crystalline β-D-gulopyranose according to this invention has been previously made, a seed crystal of β-D-gulopyranose may be added to initiate the crystallization. Otherwise, crystallization may be initiated by any known method, for instance, by scratching the side wall of the vessel.

The following examples are illustrative of the invention, but are not to be considered necessarily limitative thereof:

EXAMPLE 1

Crystalline β-D-gulopyranose was prepared by the following method:

A. Preparation of DGL-Diacetonide

A 1L, 3-necked flask equipped with a mechanical stirrer, a thermometer, a heating mantle and a condenser, was charged with acetone (600 mL), D-gulonolactone (Aldrich, 89.0 g, 0.5 mol) and 2,2-dimethoxypropane (Aldrich, 140 mL, 118.6 g, 1.14 mol). The suspension was stirred, then p-toluenesulfonic acid hydrate (1.0 g, 5 mmol) was added and the mixture was heated at reflux with a liquid temperature of 58° C.

After 4 hours at reflux, the condenser was replaced by a distillation head and the solvent was distilled from the reactor at atmospheric pressure. When the liquid temperature reached 75° C., distillation was stopped, sodium bicarbonate (5.0) was added to neutralize the acid catalyst, and the solution was stirred and allowed to cool to room temperature.

To the concentrated reaction mixture was added 400 mL of ice cold deionized water, which caused a thick precipitate to form. The off-white solid was collected by vacuum filtration and allowed to dry overnight.

The dried DGL-diacetonide (73.5 g) was dissolved in hot methanol (400 mL), filtered while hot, then cooled slowly, finally to 15° C. The crystals which formed, when isolated and dried, weighed 61.5 g. The filtrate, when concentrated to 100 mL and cooled, gave a second crop of crystals (6.5 g). The total yield of pure DGL-diacetonide was 68.0 g (53% yield). The product had a melting point of 152°-153° C. (Rosen, et al, J. Org. Chem., 49, 3994–4003 (1984) reports a melting point of 152°-154° C.).

B. Reduction of DGL-Diacetonide

A 500 mL 3-necked flask was fitted with a mechanical stirrer, a thermometer and an ice bath. The flask was charged with DGL-diacetonide (34.7 g, 0.133 mol) and 95% ethanol (173 mL) and was then cooled to 3°-5° C. Solid, powdered NaBH$_4$ (1.67 g, 0.0442 mol) was added to the reaction mixture and it was stirred vigorously. After 20 minutes, infrared (IR) analysis of the reaction mixture showed a carbonyl peak (1790 cm$^{-1}$), indicating incomplete conversion of the DGL-diacetonide. More NaBH$_4$ (0.21 g, 0.0056 mol) was added to the reaction mixture, and it was stirred for 20 more minutes in the ice water bath. An IR analysis of the mixture showed no carbonyl peak, indicating that reduction of the DGL-diacetonide was complete.

The reaction flask was then equipped with a distillation head, a condenser, a heating mantle and a vacuum takeoff. Deionized water (100 mL) was added to the reaction solution, and then, under reduced pressure (65 mm Hg), ethanol was distilled. When most of the EtOH had been removed, D-gulose diacetonide crystals began to form, and the liquid temperature began to increase. When the temperature in the distillation flask reached 39° C., the heating mantle was removed, and the reaction mixture was allowed to cool to room temperature. At this point, the D-gulose-diacetonide had crystallized as a thick mass of micro-fine needles which were collected on a Buchner funnel. The filtrate, when cooled further to 0° C. with an ice water bath, produced more crystals. These crystals were filtered off and combined with those already isolated. The final yield of crude D-gulose-diacetonide was 30.5 g or 88%.

To ensure very high purity, the crude D-gulose-diacetonide was recrystallized from water. The 30.5 g of crude D-gulose-diacetonide was dissolved in 250 mL of deionized water at 60° C. with stirring. When all the D-gulose-diacetonide had dissolved, the solution was filtered while hot, the filtrate was allowed to cool to room temperature, and the resulting crystals were filtered off. The pure, colorless D-gulose-diacetonide had a melting point of 112.5°-113° C. (Rosen, supra, reports a melting point of 113° C.).

C. Hydrolysis of L-Gulose-diacetonide

A 500 mL 5-necked flask was fitted with a mechanical stirrer, a thermometer, a heating mantle, a condenser and a vacuum takeoff. The flask was charged with D-gulose-diacetonide (15.6 g, 0.060 mol) and deionized water (200 mL). This mixture was heated to 40° C., then concentrated sulfuric acid was added dropwise until the pH of the solution was 1.5 (about 0.50 g was required). The temperature was maintained at 48° C., and the pressure inside the flask was reduced to 75 mm Hg in order to remove acetone as it was formed. The reaction was allowed to proceed in this way for 6 hours.

After hydrolysis was complete, the reaction mixture was neutralized by passing it through a column of Duolite A-340 weak base ion exchange resin (Rohm and Haas, 50.0 mL, free base form).

The eluant was concentrated in a rotary evaporator to give a syrup (13.0 g) that contained 10.0 g (0.056 mol, 77% dissolved solids) of D-gulose, for a yield of 92.6% based on diacetonide charged. HPLC analysis of the product showed D-gulose (98.2%) and L-sorbitol (0.8%).

E. Crystallization of β-D-Gulopyranose from Ethanol

The syrup from step C was diluted with an equal volume of absolute ethanol and stirred at room temperature. A seed crystal of β-D-gulopyranose was added to initiate the crystallization, which was complete after about two hours. The first crop provided a 73% yield of crystals based on solids charged. The filtrate was concentrated again to 80% solids, diluted with ethanol, and seeded to harvest a second crop of crystals. The melting point of the dried crystals was 130°-132° C. HPLC analysis of the crystals indicated >99.9% β-D-gulopyranose.

E. Crystallization of β-D-Gulopyranose from Water

The syrup from step C was seeded with a few crystals of β-D-gulopyranose. The crystals were allowed to grow overnight at room temperature, then the mixture was cooled in a refrigerator for an additional 24 hours to complete the crystallization. The crystals were collected by filtration and dried in vacuo. The melting point of the dried crystals was 130°-132° C. HPLC analysis of the crystals indicated >99.9% β-D-gulopyranose.

EXAMPLE 2

The physical properties of crystalline β-D-gulopyranose prepared using the procedure set forth in Example 1 were determined by conventional methods and found to be as follows:

A. Melting Point

The crystalline β-D-gulopyranose was found to have a sharp melting point of 130°-132° C. A sharp melting point is a known indicator of the purity of a crystalline substance.

B. Elemental Analysis

The elemental analysis of crystalline β-D-gulopyranose was as follows:

| | | | Calculated (%) | Found (%) |
|---|---|---|---|---|
| $C_6H_{12}O_6$ | MW 180.16 | C | 40.00 | 39.80 |
| | | H | 6.72 | 6.53 |
| | | N | 0.0 | 0.0 |
| | | O | 53.29 | 52.50 |

C. Mutarotation of Crystalline β-D-Gulopyranose

Most crystalline monosaccharides mutarotate, i.e., their optical rotation changes with time as the single anomeric form present in the crystal equilibrates with other forms in solution. The mutarotation of crystalline β-D-gulopyranose was determined as follows:

Crystalline β-D-gulopyranose (10.00 g) was dissolved in 50.0 mL deionized water, then the solution was transferred quickly to a 20 cm polarimeter tube. The change in optical rotation (α) was monitored with time:

| minutes | α | $[α]_D$ | $\ln\Delta[α]_D$ |
|---|---|---|---|
| 0.0 | — | — | — |
| 2.3 | −14.8 | −37 | −2.485 |
| 4.3 | −14.0 | −35 | −2.303 |
| 6.3 | −13.5 | −33.75 | −2.169 |
| 11.3 | −12.9 | −32.25 | −1.981 |
| 15.3 | −12.0 | −30.0 | −1.609 |
| 22.8 | −11.4 | −28.5 | −1.253 |
| 30.0 | −10.9 | −27.25 | −0.811 |
| 37.5 | −10.5 | −26.25 | −0.223 |
| 43.0 | −10.4 | −26.0 | 0.0 |
| 55.0 | −10.2 | −25.5 | 0.693 |
| 66.0 | −10.1 | −25.25 | — |
| 94.0 | −10.0 | −25.0 | — |
| 140.0 | −10.0 | −25.0 | — |
| 380.0 | −10.0 | −25.0 | — |

FIG. 1 shows a plot of $[α]_D$ versus time for β-D-gulopyranose.

D. Optical Rotation of Crystalline β-D-Gulopyranose

Figure 2:
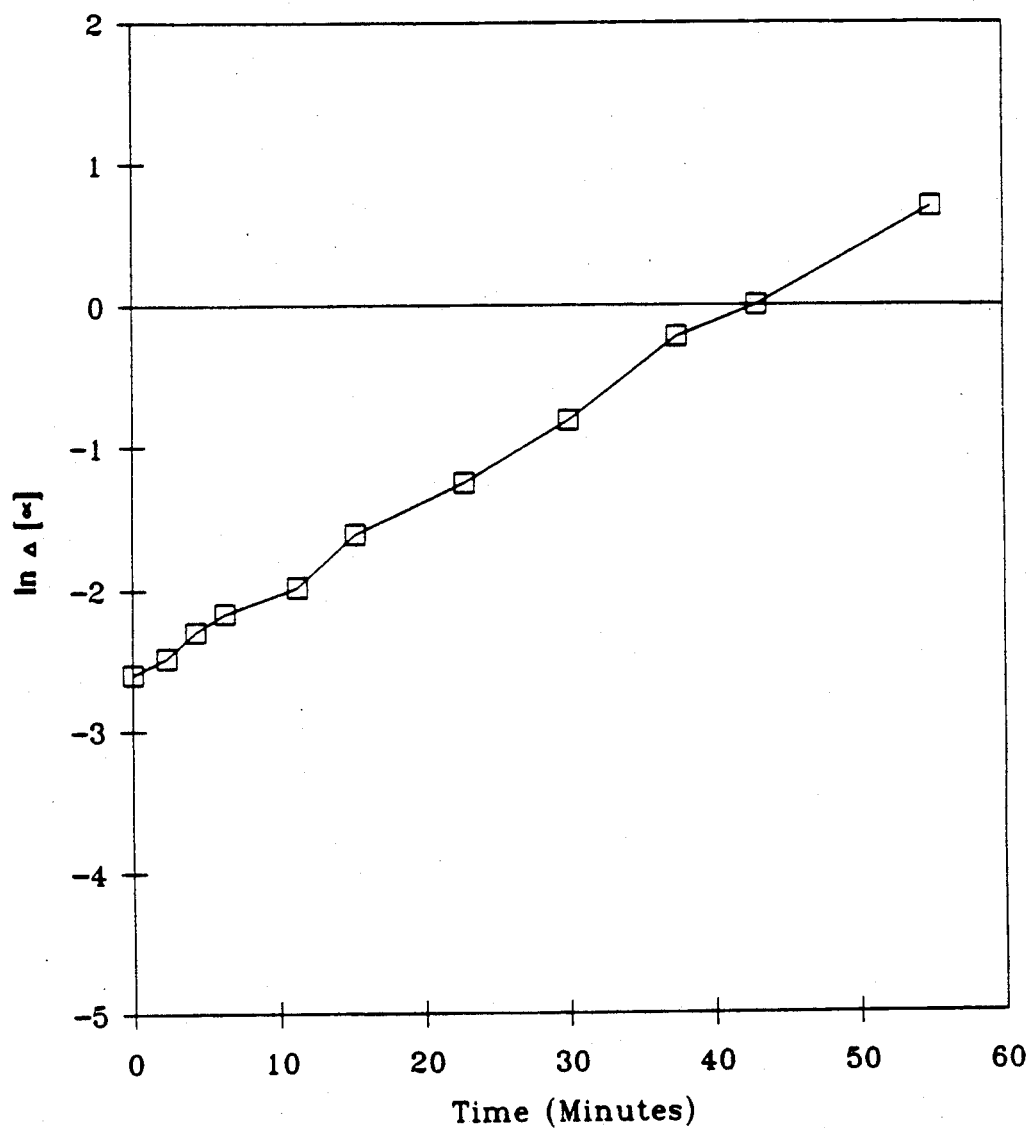
FIG. 2 shows a plot of ln Δ[α]$_D$ versus time for the mutarotation of β-D-gulopyranose. This plot is used to calculate the specific optical rotation of crystalline β-D-gulopyranose.

The specific optical rotation of the crystalline anomer can be calculated using the mutarotation data. FIG. 2 shows a first order plot (ln $\Delta[α]_D$ versus time) of the mutarotation. Calculating anti ln at time=0 yields the value −40 degrees. Because only a single isomer is present, the specific rotation of crystalline β-D-gulopyranose (−40°) is higher than any value which has been reported previously for syrupy D-gulose.

We claim:
1. A composition consisting essentially of crystalline β-D-gulopyranose, characterized by a sharp melting point of 130°-132° C.
2. The composition consisting essentially of crystalline β-D-gulopyranose of claim 1, further characterized by an initial specific optical rotation of about −40°.
3. A composition consisting essentially of crystalline β-D-gulopyranose, characterized by a sharp melting point of 130°-132° C., and an initial specific optical rotation of about −40°.
4. A method for forming a composition consisting essentially of crystalline β-D-gulopyranose from D-gulose syrup contained in a vessel comprising the steps:
   initiating formation of a composition consisting essentially of β-D-gulopyranose crystals, and isolating the composition consisting essentially of β-D-gulopyranose crystals from the syrup.
5. The method of claim 4 further comprising the step: diluting the D-gulose syrup with ethanol.
6. The method of claim 4 further comprising the step: diluting the D-gulose syrup with water.
7. The method of claim 4 wherein initiation of formation of a composition consisting essentially of β-D-gulopyranose crystals is by the step:
   adding a β-D-gulopyranose seed crystal to the syrup.
8. The method of claim 4 wherein initiation of formation of a composition consisting essentially of β-D-gulopyranose crystals is by the step:
   scratching the wall of the vessel which contains the syrup.

* * * * *